(12) United States Patent
Hardarson et al.

(10) Patent No.: US 12,098,657 B2
(45) Date of Patent: Sep. 24, 2024

(54) HEAT INTEGRATION

(71) Applicant: CRI, HF, Kopavogur (IS)

(72) Inventors: Björn Hardarson, Reykjavik (IS);
Ólafur Hrafn Björnsson, Reykjavík (IS); Emeric Sarron, Paris (FR);
Armen Eduardo Kodjaian, Buenos Aires (AR)

(73) Assignee: CRI, HF, Kopavogur (IS)

( * ) Notice: Subject to any disclaimer, the term of this patent is extended or adjusted under 35 U.S.C. 154(b) by 0 days.

(21) Appl. No.: 18/161,297

(22) Filed: Jan. 30, 2023

(65) Prior Publication Data

US 2023/0243279 A1    Aug. 3, 2023

Related U.S. Application Data (60) Provisional application No. 63/305,392, filed on Feb. 1, 2022.

(51) Int. Cl.
| | |
|---|---|
| *F01K 23/06* | (2006.01) |
| *F01K 7/38* | (2006.01) |
| *F01K 9/00* | (2006.01) |

(52) U.S. Cl.
CPC .............. *F01K 23/064* (2013.01); *F01K 7/38* (2013.01); *F01K 9/00* (2013.01)

(58) Field of Classification Search
CPC ..... B01D 3/007; C07C 29/1518; C07C 31/04; F01K 23/064; F01K 7/38; F01K 7/44; F01K 9/00; F22D 1/325
See application file for complete search history.

(56) References Cited

U.S. PATENT DOCUMENTS

| | | |
|---|---|---|
| 2,549,290 A | 4/1951 | Congdon et al. |
| 2,727,367 A | 12/1955 | Claude |

(Continued)

FOREIGN PATENT DOCUMENTS

| | | |
|---|---|---|
| CA | 2354927 A1 | 2/2002 |
| CN | 108779051 B | 1/2022 |

(Continued)

OTHER PUBLICATIONS

Al Fadli, A.M., et al. "Simulation of Transients in a Multi Bed Adiabatic Methanol Synthesis Reactor" Published in the Fourth Saudi Engineering Conference, vol. 5, pp. 121-127, Nov. 30, 1995.

(Continued)

*Primary Examiner* — Jesse S Bogue
(74) *Attorney, Agent, or Firm* — Workman Nydegger (57) ABSTRACT

A method for heat integration between a chemical synthesis plant that runs an exothermic reaction and (ii) and a partner plant that generates a working fluid such as steam (e.g., runs a power cycle). The present disclosure describes both internal and external heat integration. Internal heat integration may provide heat from the exothermic reaction (e.g., from methanol synthesis) to a reboiler associated with a distillation column of the chemical synthesis plant. External heat integration may use heat from the exothermic reaction to preheat a condensed water stream (which stream is downstream from the turbine and condenser of the power cycle). Such reduces the need for bleed off the turbine to preheat condensed water as part of the power cycle. A bleed off the turbine provides heat to the reboiler associated with the distillation column of the chemical synthesis plant. Heat integration provides overall improved energy use within both plants.

20 Claims, 8 Drawing Sheets

(56) References Cited

U.S. PATENT DOCUMENTS

| | | | |
|---|---|---|---|
| 3,872,025 A | 3/1975 | Singleton | |
| 3,918,934 A | 11/1975 | Kriebel et al. | |
| 3,979,183 A | 9/1976 | Scott | |
| 4,134,732 A * | 1/1979 | Jackson | B01D 3/143 203/DIG. 16 |
| 4,149,940 A * | 4/1979 | Pinto | C07C 29/1518 203/DIG. 19 |
| 4,249,907 A | 2/1981 | Callejas | |
| 4,272,823 A | 6/1981 | Pool | |
| 4,372,755 A | 2/1983 | Tolman et al. | |
| 4,428,799 A | 1/1984 | Standiford | |
| 4,626,552 A | 12/1986 | Arcuri | |
| 4,717,409 A | 1/1988 | Atkinson | |
| 5,346,593 A * | 9/1994 | Cialkowski | B01D 3/146 203/99 |
| 5,715,706 A | 2/1998 | Rathbone | |
| 6,494,996 B2 * | 12/2002 | Gilbert | C07C 29/82 203/14 |
| 6,905,592 B2 | 6/2005 | Bence et al. | |
| 6,958,135 B1 | 10/2005 | Filippi et al. | |
| 7,122,149 B2 | 10/2006 | Li et al. | |
| 7,144,923 B2 | 12/2006 | Fitzpatrick | |
| 7,347,978 B2 | 3/2008 | Lomax et al. | |
| 7,353,847 B2 | 4/2008 | Early | |
| 7,470,811 B2 | 12/2008 | Thiebaut | |
| 7,479,468 B2 | 1/2009 | Van Egmond et al. | |
| 7,790,775 B2 | 9/2010 | Early | |
| 7,968,610 B2 | 6/2011 | Tasso et al. | |
| 8,084,652 B2 * | 12/2011 | Littleford | B01D 53/1418 568/888 |
| 8,729,141 B2 | 5/2014 | Bae et al. | |
| 8,772,360 B2 * | 7/2014 | Allam | B01J 19/0053 518/703 |
| 8,806,870 B2 * | 8/2014 | Hirata | F23J 15/04 60/648 |
| 9,283,531 B2 | 3/2016 | Banerjee et al. | |
| 9,574,829 B2 * | 2/2017 | Yang | B01D 3/007 |
| 10,016,699 B2 | 7/2018 | Wakabayashi et al. | |
| 10,227,901 B2 * | 3/2019 | Bergins | F01K 23/18 |
| 10,960,349 B2 | 3/2021 | Sarron et al. | |
| 11,369,932 B2 | 6/2022 | Sarron | |
| 11,603,342 B2 | 3/2023 | Urakawa et al. | |
| 2002/0113228 A1 | 8/2002 | Kim et al. | |
| 2006/0248890 A1 * | 11/2006 | Iijima | F01K 25/065 423/437.1 |
| 2007/0280862 A1 | 12/2007 | Davis et al. | |
| 2008/0217489 A1 | 9/2008 | Higbee | |
| 2009/0077866 A1 | 3/2009 | Kalnes et al. | |
| 2009/0188867 A1 | 7/2009 | Vuong et al. | |
| 2011/0209407 A1 | 9/2011 | Arya et al. | |
| 2015/0068205 A1 | 3/2015 | Goto et al. | |
| 2015/0202547 A1 | 7/2015 | Wakabayashi et al. | |
| 2016/0017800 A1 | 1/2016 | Simpson | |
| 2016/0237858 A1 * | 8/2016 | Bergins | F01K 25/103 |
| 2017/0320796 A1 | 11/2017 | Lee et al. | |
| 2018/0119023 A1 | 5/2018 | Eizenga et al. | |
| 2018/0187573 A1 | 7/2018 | Gutscher | |
| 2020/0207689 A1 | 7/2020 | Urakawa et al. | |
| 2021/0197121 A1 | 7/2021 | Sarron et al. | |
| 2021/0363079 A1 | 11/2021 | Tjarnehov et al. | |
| 2022/0226795 A1 | 7/2022 | Jonsson et al. | |
| 2022/0401904 A1 | 12/2022 | Sarron | |

FOREIGN PATENT DOCUMENTS

| | | |
|---|---|---|
| EP | 0135357 A2 | 3/1985 |
| EP | 2831025 A1 | 2/2015 |
| EP | 3416936 B1 | 3/2021 |
| EP | 3835556 A1 | 6/2021 |
| FR | 2583988 A1 | 1/1987 |
| GB | 1316705 A | 5/1973 |
| GB | 2158435 A | 11/1985 |
| GB | 2461723 A | 1/2010 |
| KR | 10-2015-0086198 A | 7/2015 |
| WO | 2007/108014 A1 | 9/2007 |
| WO | 2013/144041 A1 | 10/2013 |
| WO | 2013171239 A1 | 11/2013 |
| WO | 2018/107170 A1 | 6/2018 |

OTHER PUBLICATIONS

Al-Kabani et al., Comparative energetic assessment of methanol production from CO2: Chemical versus electrochemical process. (2016), Applied Energy, 1-13, 165.

Bremer, Jens, et al. "CO2 Methanation: Optimal Start-Up Control of a Fixed-Bed Reactor for Power-to-Gas Applications" Published in Process Systems Engineering, 22 pages, Sep. 2, 2016.

Carl Schaschke, Dictionary of Chemical Engineering, 2014, Oxford University Press, Retrieved from https://app.knovel.com/hotlink/pdf/id:ktO0TW6WYC/dictionary-chemical-engineering/ specific.

International Search Report from PCT Application No. PCT/IB2018/059633.

Kazemi et al., Evaluation of Different Vapor Recompression Distillation Configurations Based on Energy Requirements and Associated Costs, Applied Thermal Engineering, 305-313, 94.

Perez-Fortes et al., Methanol synthesis using captured CO2 as raw material: Techno-economic and environmental assessment. (2016), Applied Energy, 718-732, 161.

Shahrokhi, M., et al. "Modeling, Simulation and Control of a Methanol Synthesis Fixed-Bed Reactor," Published in Chemical Engineering Science vol. 60, pp. 4275-4286, Apr. 18, 2005.

International Search Report from Corresponding International Application No. PCT/IB2023/050801, May 11, 2023.

* cited by examiner

HEAT INTEGRATION

CROSS REFERENCE TO RELATED APPLICATION(S)

This application claims the benefit of priority under 35 U.S.C 119(e) to U.S. Provisional Application No. 63/305,392, filed Feb. 1, 2022, titled HEAT INTEGRATION, the entire contents of which are incorporated herein by reference.

FIELD OF THE DISCLOSURE

The disclosure relates to heat integration between processes that are typically not related to one another, as well as systems and methods for implementing or operating such systems. By way of example, such integration may be between (i) a plant that generates steam (or another working fluid) associated with a power cycle (e.g., using a steam turbine or other working fluid turbine to generate electricity) in connection with (ii) a chemical synthesis plant that produces heat from an exothermic reaction. The system may exchange heat between such plants, to better maximize efficiency, reduce waste heat, reduce cooling load, etc. It will be apparent that there may be instances, especially green field sites, where steam or another working fluid may not be used to produce electricity, but used for other purposes. For example, there may be sites with waste heat from industry, where it is more economical to use all the heat as thermal energy, or where steam (or another working fluid) may be used to produce mechanical (rather than electrical) work. Integration as described herein with an electrical power generation plant is therefore merely exemplary. Such integration may be referred to as external integration. Internal heat integration, e.g., within a plant is also described.

BACKGROUND

Global climate change has been deemed to be the "most pressing environmental challenge of our time." The National Aeronautics and Space Administration (NASA) cites that "scientific evidence for warming of the climate system is unequivocal." Climate change results from the warming effects of greenhouse gases such as water vapor, nitrous oxide, methane, and carbon dioxide. In addition to concerns over climate change, there is a continuing need for improved efficiency in the generation and overall efficient use of energy. For example, a wide variety of power plants for generating electricity for the electrical grid rely on generation of steam (or another working fluid) through various means (e.g., combustion of fossil or other fuels, geothermal, etc.), which steam or other working fluid is used in a Rankine or other thermodynamic power cycle, running a turbine to generate electricity. In a typical power cycle, a portion of the generated steam (or another working fluid) is bled off the turbine (e.g., as a low or medium pressure bleed), for use in reheating the feedwater stream after it has passed through the turbine and condenser, to prepare the feedwater to be cycled through the cycle again.

At the same time, there are numerous unrelated chemical synthesis and other processes that involve exothermic reactions, where cooling water must be provided, to absorb heat generated during such exothermic synthesis or similar processes. Because such processes are not typically related to power generation processes that run a Rankine or other thermodynamic power cycle, such processes typically operate independently of one another, e.g., often significant distances apart from one another, with no practical way of integrating heat between such processes. The present disclosure relates to practical methods and applications for integration of heat between such processes, which can decrease the need for any low or medium pressure bleed stream off the turbine within the power generation process in order to preheat the condensate for cycling again, while also reducing the need for cooling water necessary for absorbing heat generated by the exothermic reaction associated with a chemical synthesis process.

Such integration can increase the efficiency of both processes being integrated together, making better overall use of energy resources, and making both processes more environmentally friendly.

SUMMARY

The present disclosure is directed to systems and methods that provide for improved use of heat energy between typically unrelated processes (e.g., processes which do not otherwise share or exchange material streams), by integrating heat between them. For example, in one specific implementation, a CRI ETL plant (Applicant's emissions to liquid (ETL) plant) that converts $CO_2$ emissions and hydrogen (e.g., from water electrolysis) to produce methanol can be integrated with a power generation plant (e.g., a power generation plant including a thermodynamic power cycle). Such an ETL plant could be integrated with other processes, as well. Waste heat from the ETL plant, which is generated due to methanol synthesis being an exothermic reaction is utilized in the power cycle of the power generation plant, e.g., to preheat the condensate coming off the turbine, prior to boiling and converting the condensate back into steam (or other vaporized working fluid), for reintroduction to the turbine. The two plants may be further integrated where a portion of the generated steam (or another working fluid) is diverted from the power cycle (e.g., rather than being used in the turbine for electrical power generation), and instead utilized in the ETL process as a heating medium. Thus the thermal energy associated with a portion of the steam (or another working fluid) is used for energy distribution purposes in the ETL plant, instead of the steam (or another working fluid) going through the turbine to produce electricity. Such energy distribution may take one of many forms. For example, in addition to use for a heating purpose (e.g., as part of a distillation process), such steam (or another working fluid) could also be used for driving mechanical equipment (e.g., a syngas compressor and/or circulator) within the ETL or other chemical synthesis plant. Use in mechanical equipment would convert the thermal energy to mechanical energy. In any case, such integration makes sense and is beneficial where there is a synergy of temperature ranges between the needs of one process, relative to what is available from the other process. For example, what is suitable for pre-heating in the thermodynamic cycle power generation process coincides with the waste heat temperature from the chemical synthesis process, and vice versa relative to the steam or other working fluid from the turbine relative to the needs of the reboiler of the distillation column (and/or the carbon capture unit or other unit) of the chemical synthesis plant.

Such integration is beneficial because the efficiency achieved when producing electricity from steam (or another working fluid), (e.g., via expansion through a turbine) is relatively low—e.g., less than 40%. Where a portion of the working fluid stream is instead diverted to the ETL plant, e.g., for use in providing heat to a reboiler associated with a distillation column, a significantly greater efficiency of energy use within such working fluid is achieved, as heat transfer in a heat exchanger can be achieved at far higher energy efficiency than converting such working fluid to electrical energy (e.g., and then using electrical power to generate steam or other working fluid for heating the reboiler). While in many plants electricity would not be used to generate steam (e.g., a fuel-powered boiler would likely be more cost effective), in the present CRI ETL plant, it is desirable to minimize the $CO_2$ footprint, by using green electricity. In any case, the present integration systems propose an alternative route, eliminating the need for a steam or other working fluid generator at all (e.g., by integrating steam (or another working fluid) from the power generation plant or other partner plant). While the reboiler of the distillation portion of the chemical synthesis plant is one specific example of where such steam (or another working fluid) may be used, it will be apparent that such heated working fluid may also be used elsewhere. By way of further example, another relevant use for the steam or other working fluid is in a $CO_2$ capture unit (e.g., stripper) of an ETL plant, or other similar use in another chemical synthesis plant.

Both plants benefit from such heat integration. For example, the electrical power generation plant benefits as the steam or other working fluid provided to the ETL or other chemical synthesis plant has greater value to the ETL or other chemical synthesis plant, than to the electrical power generation plant. Waste heat provided from the chemical synthesis plant to the electrical power generation plant is beneficial to the power generation plant, as it reduces the amount of working fluid that must be bled off the turbine for reheating the condensate coming out of the turbine and condenser, actually increasing the power that is generated by the turbine (as more steam or other working fluid is available for power generation). The increase in turbine power output can potentially be larger than what the exergy content of the waste heat provided would suggest, if the exergy content of the replaced bleed steam (or other working fluid) is higher than that of the waste heat. Even where some portion of the working fluid may be diverted to the ETL plant for heating purposes (e.g., in the distillation system, $CO_2$ capture unit, or the like), overall efficiency of the processes is improved, as will be shown in the examples. The ETL plant benefits in a reduced need for cooling water, as well as elimination of any need for a steam or other working fluid generator (as the needed steam or other working fluid is provided directly from the electrical power generation plant). The overall integrated system exhibits improved use of energy, as compared to each process operating independently. A chemical synthesis plant, such as one that converts $CO_2$ emissions into liquid fuels (e.g., methanol) or other useful chemical products is particularly well suited to integration with a power generation plant, or any other plant that may generate steam or another working fluid (e.g., as part of a thermodynamic power cycle), as the chemical synthesis plant (e.g., Applicant's ETL process) as contemplated in one particular embodiment can use $CO_2$ flue gases from the partner plant as feedstock material for use in synthesis of a value added chemical product (e.g., methanol which can be used as a fuel, a chemical feedstock for use in other chemical processes, as enzyme feed for the production of a variety of compounds such as proteins or in a wide variety of other applications).

By trading the waste heat from the ETL or another chemical synthesis plant for steam or other working fluid from the partner plant operating a power cycle, the waste heat from the ETL or another chemical synthesis plant can be used to preheat condensate from the turbine and condenser of the power cycle, and the portion of diverted working fluid from the partner plant running a power cycle can be used to provide heat to the reboiler of a distillation column associated with the ETL or other chemical synthesis plant, to run mechanical equipment (e.g., compressors, etc.) and/or to provide thermal energy for the $CO_2$ capture unit (e.g., stripper) or other units. Both plants benefit from such heat integration.

The heat integration embodiments described herein are not limited to embodiments where one of the plants runs a methanol synthesis process. A wide variety of chemical synthesis or similar processes that provide waste heat in the desired temperature range (e.g., at least 80° C., such as from 80° C. to 200° C., or from 100° C. to 150° C.) due to an exothermic chemical reaction could be used. Similarly, the partner plant could be one of a wide variety, of plants, so long as it includes a thermodynamic cycle or similar process that generates a high thermal value working fluid stream, and has a need to preheat a condensate (e.g., from a turbine and condenser). An important characteristic of the present embodiments for heat integration is that the temperature provided by the waste heat is matched to the need for preheating the condensate.

The present disclosure also describes examples of internal heat integration, within a given plant (e.g., an ETL plant). Such an exemplary plant system may include two teed streams where the first feed stream contains water from which hydrogen is produced in an electrolysis unit, and the second feed stream comprises $CO_2$. An electrolysis unit, a $CO_2$ capture unit, one or more compressors, one or more heat exchangers, a reactor, and a catch pot may be provided. The system may further include a catch pot top fraction, a distillation column, a condenser, a reflux stream, a distillate stream (e.g., sent to storage), a reboiler, and a source of steam or another working fluid for example, from an electric steam generator. Another exemplary system may include a reboiler for reheating a bottoms condensate fraction from a distillation column, a pump, first and second heat exchangers, where the reboiler supplies a cold stream to the pump, which supplies the cold stream to the first heat exchanger. The first heat exchanger is connected to an outlet of a reactor within which an exothermic reaction is conducted. An outlet stream from the first heat exchanger is heated to an increased temperature relative to the cold stream and is fed to the second heat exchanger for further heating of the stream to a desired temperature before being fed to the reboiler.

Such a system may be an emissions to liquid (ETL) plant.

The exothermic reaction conducted in the reactor may be a methanol synthesis reaction.

The second heat exchanger may use steam or another working fluid to produce the hot output stream.

Specific methods, embodiments, and variations of the system are described in greater detail in the following discussion.

These and other features, aspects, and advantages of the present disclosure will become readily apparent and better understood in view of the following description, appended claims, and accompanying drawings.

BRIEF DESCRIPTION OF THE DRAWINGS

FIGS. 1A-1B are simplified diagrams of an exemplary thermodynamic power cycle shown before heat integration (FIG. 1A) and after heat integration (FIG. 1B) according to the present disclosure, showing how waste heat from an ETL process (or from another process with available waste heat)

can be integrated into the thermodynamic power cycle, decreasing the need for preheating steam or other working fluid bleed, so as to increase electrical power generation.

The drawing figures are not necessarily drawn to scale, but instead are drawn to provide a better understanding of the components, and are not intended to be limiting in scope, but to provide exemplary illustrations.

The figures illustrate exemplary configurations of heat integration systems and associated facilities, and are not meant to limit the structures, configurations, or functions of heat or working fluid integration systems and associated facilities embodiments according to the present disclosure.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are shown in the drawings and will be described below. It should be understood, however, there is no intention to limit the disclosure to the embodiments disclosed, but on the contrary, the intention is to cover all modifications, alternative constructions, combinations, and equivalents falling within the spirit and scope of the disclosure and defined by the appended claims.

It will be understood that, unless a term is defined in this patent to possess a described meaning, there is no intent to limit the meaning of such term, either expressly or indirectly, beyond its plain or ordinary meaning.

All heat exchangers described herein may be of any suitable heat exchanger configuration having any suitable properties and operated in any suitable manner. By way of non-limiting example, any given heat exchanger may be a parallel-flow heat exchanger, counter-flow heat exchanger, finned or unfinned tubular heat exchanger, shell-and-tube heat exchanger, U-tube heat exchanger, single-pass straight heat exchanger, two-pass straight heat exchanger, plate or frame heat exchanger, plate-fin heat exchanger, microchannel heat exchanger, or otherwise.

Heat integration as a general term will be used to mean any process by which heat from one process or system is introduced into another process or system. The heat integration described in the present embodiments may be internal, meaning within a single independent system or process, or external, meaning that the heat from one independent system or process is introduced into another independent process or system. By independent, it is meant that the system or process can be (and typically would be) conducted independently from, and without regard or integration with the other system or process (e.g., no exchange of material streams required between such processes). An example of such independent processes and systems that can be heat integrated is a power generation system or process running a thermodynamic power cycle, and an exothermic chemical synthesis system or process. Both such processes can (and typically are) conducted independently of one another, although the present disclosure teaches how heat from each process or system can be integrated into the other process or system, providing an overall improved efficiency and use of energy.

As used herein, reference to a Rankine cycle or another thermodynamic power cycle is to be construed broadly, referring to a variety of thermodynamic processes for producing usable work (e.g., in the form of generated electrical power). A typical thermodynamic power cycle includes a steam or other working fluid generator (e.g., boiler), a turbine, a condenser, a pump, and a water pre-heater, as shown in the Figures. As noted herein, the present embodiments of heat integration are not limited to instances where a thermodynamic power cycle actually generates electricity, but is to be broadly construed, to include any of various cycles that involve the generation of steam or other heated working fluid (where such steam or other working fluid can be used to provide any of a wide variety of functions (e.g., heating, mechanical work, electrical power generation, etc.)

Although an emissions to liquid (ETL) plant which converts carbon dioxide and hydrogen (e.g., from water electrolysis) into methanol is principally described in the present embodiments as one of the plants used in the present heat integration processes, it will be appreciated that other plants characterized by an exothermic chemical reaction (so as to have available waste heat) and a need for cooling (e.g., cooling water) may also be suitable candidates. For example, other types of chemical synthesis plants that conduct exothermic reactions as part of product synthesis, particularly those that employ a flue gas $CO_2$ stream as a reactant material used in product synthesis may be suitable candidates for heat integration.

Similarly, an electrical power generation plant is principally described in the present embodiments as the other plant (i.e., the partner plant) used in the present heat integration processes. Even so, it will be appreciated that other plants that similarly run a thermodynamic power cycle (so as to have available steam or other working fluid) and exhibit a need for reheating water (or other cycle fluid) coming from the condenser following the turbine may also be suitable candidates. For example, a wide variety of plants that include a power cycle turbine for electrical power generation may be suitable candidates for heat integration, whether electrical power generation is their principal purpose or not (e.g., co-generation plants, which may generate electricity for the grid or internal electrical needs as a secondary purpose may also be suitable candidates). For example, one specific non-limiting example of such a co-generation plant is a ferrosilicon plant.

This process of integrating heat sources and needs for heat between two such normally independent plants is beneficial, as it increases the overall efficiency of energy use, e.g., decreasing the need for cooling water in the ETL or other chemical synthesis plant (which needs significant cooling due to its exothermic synthesis reaction), while also increasing the electrical output of the electrical generation plant, as waste heat from the ETL or other chemical synthesis plant is used to preheat the water coming out of the condenser of the power cycle. In a similar manner, a portion of the steam or other working fluid generated as part of the power cycle can be diverted to the ETL or other chemical synthesis plant, which needs a high value heat stream (more than can be provided by capturing heat from the ETL's exothermic reaction) to heat material in the reboiler associated with the distillation column of the ETL plant, for use in the $CO_2$ capture unit (e.g., stripper) of the ETL plant or for use in the $H_2$ generation (e.g., electrolysis) unit, etc.

The benefits are twofold for the power cycle: on the one side, receiving the preheat energy from the ETL or other chemical plant running an exothermic synthesis reaction allows more of the steam or other working fluid to be used for electrical generation, instead of being used for heating, thus making the plant more productive. Secondly, the heat addition is such that the conversion efficiency of the cycle itself increases, therefore producing more electricity from the same energy. While the ETL or other chemical synthesis plant may generate heat of a sufficient quality (i.e., high enough temperature) to be used internally, it may not produce enough of such a waste heat stream, meaning that importation of additional heat is required. That said, there is leftover waste heat, which is too low in temperature to be used in the ETL or other chemical synthesis plant, but this lower grade waste heat can be used in the power cycle as described. As such, the cycle can be seen as acting as a surrogate heat pump for the ETL or other chemical synthesis plant, turning low-value heat into higher-value heat (e.g., high temperature steam).

Figure 5A:
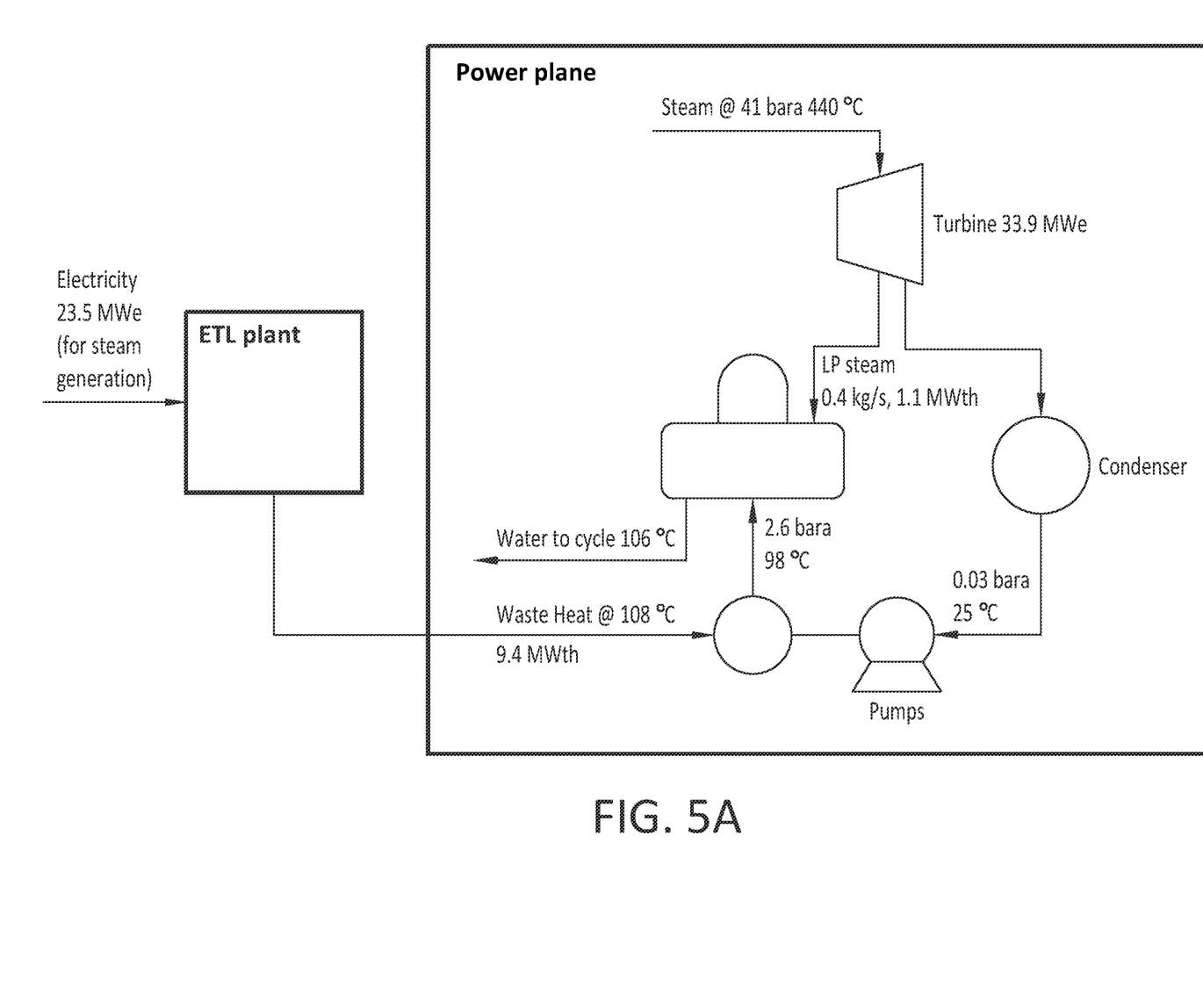
FIG. 5A illustrates a specific example of waste heat integration, showing an increase in power generation that can be achieved, compared to the baseline configuration of FIG. 1A that includes no heat integration.

As shown in the examples, in an implantation, the electrical generation plant is able to generate more electricity (e.g., a 5-6% increase) than if the processes were operated independently, because of the preheating of the condenser water, which benefit is received by the electrical generation plant from the ETL plant. Such an example is based on heat integration from the ETL plant to the electrical generation plant, with no working fluid (e.g., steam) being diverted from the electrical generation plant to the ETL plant (e.g., as shown in FIG. 5A). Other examples are also provided (FIG. 5B-5C), where a portion of the steam or other working fluid is diverted from the electrical generation plant to the ETL plant (e.g., FIG. 5B), or where steam or other working fluid is diverted from the electrical generation plant to the ETL plant, and waste heat is diverted from the ETL plant to the electrical generation plant (FIG. 5C). In such examples, the amount of diverted steam or other working fluid is of more value to the ETL plant than it is to the electrical generation plant, and the diverted waste heat from the ETL plant is of more value to the electrical generation plant than to the ETL plant. Overall efficiency of both plants is improved by heat integration therebetween as described herein. For example, this is true because of the large amount of thermodynamic energy required to convert liquid water to steam (a phase change), without a change in temperature. In the present case, heat is used efficiently in either of the two physical states of water without having to waste energy converting from one state to the other (i.e. liquid to gas).

Figure 1A:
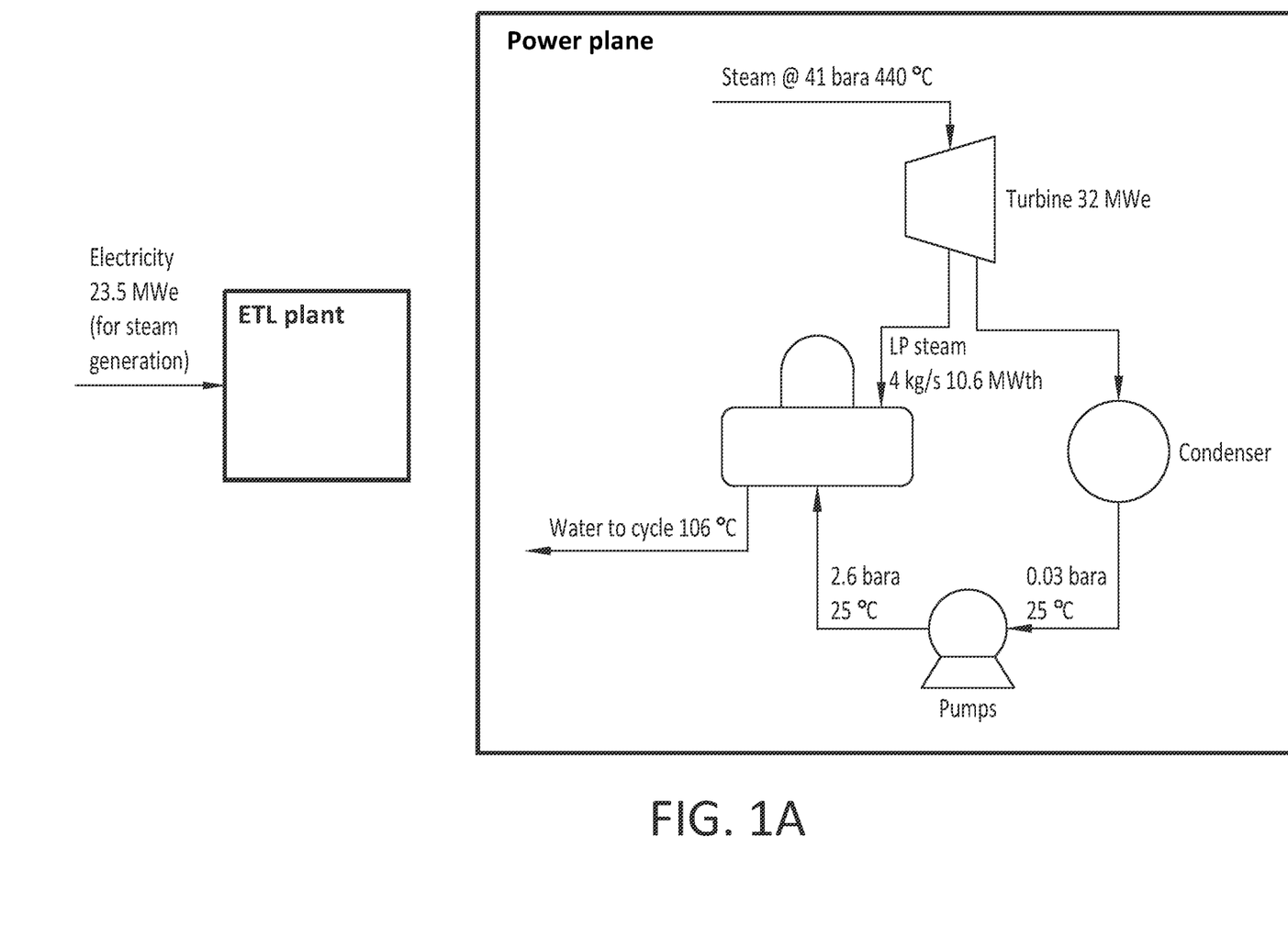

FIG. 1A shows an exemplary operational scheme for an exemplary electrical generation plant, generating electrical power through a conventional thermodynamic power cycle. As shown, steam or other working fluid can be provided under pressure (e.g., 41 bara and 440° C.) into the turbine to generate electrical power (e.g., 32 MW at full load). Spent steam or other working fluid exiting the turbine is sent to the condenser, where it is further cooled and condensed (e.g., to 25° C.). It will be apparent that the actual cooled condensate temperature may vary widely, depending on location and climate, the type of turbine used, and other factors, such that a value of 25° C. is merely exemplary. Such condensed water is then pumped to the feedwater heater, where it is heated using a low pressure (LP) or medium pressure (MP) bleed stream from the turbine, to preheat the condensed water (e.g., up to 106° C.). The preheated water is then sent to a steam or other working fluid generator (i.e., boiler) (not shown), where it is further heated to the conditions desired at entrance of the turbine (e.g., 41 bara and 440° C.), and the process begins again. In the operational scheme shown in FIG. 1A, the preheating LP bleed stream is shown as being provided at a flow rate of 4 kg/s, which is what is needed to preheat the given flowrate of water from 25° C. to 106° C. FIG. 1A also shows the independently operated ETL plant, which requires 23.5 MW of electrical power (assuming 98% efficiency) for steam generation. The net electricity export of these two systems when operated independently as shown in FIG. 1A is 32−23.5=8.5 MWe.

Figure 1B:
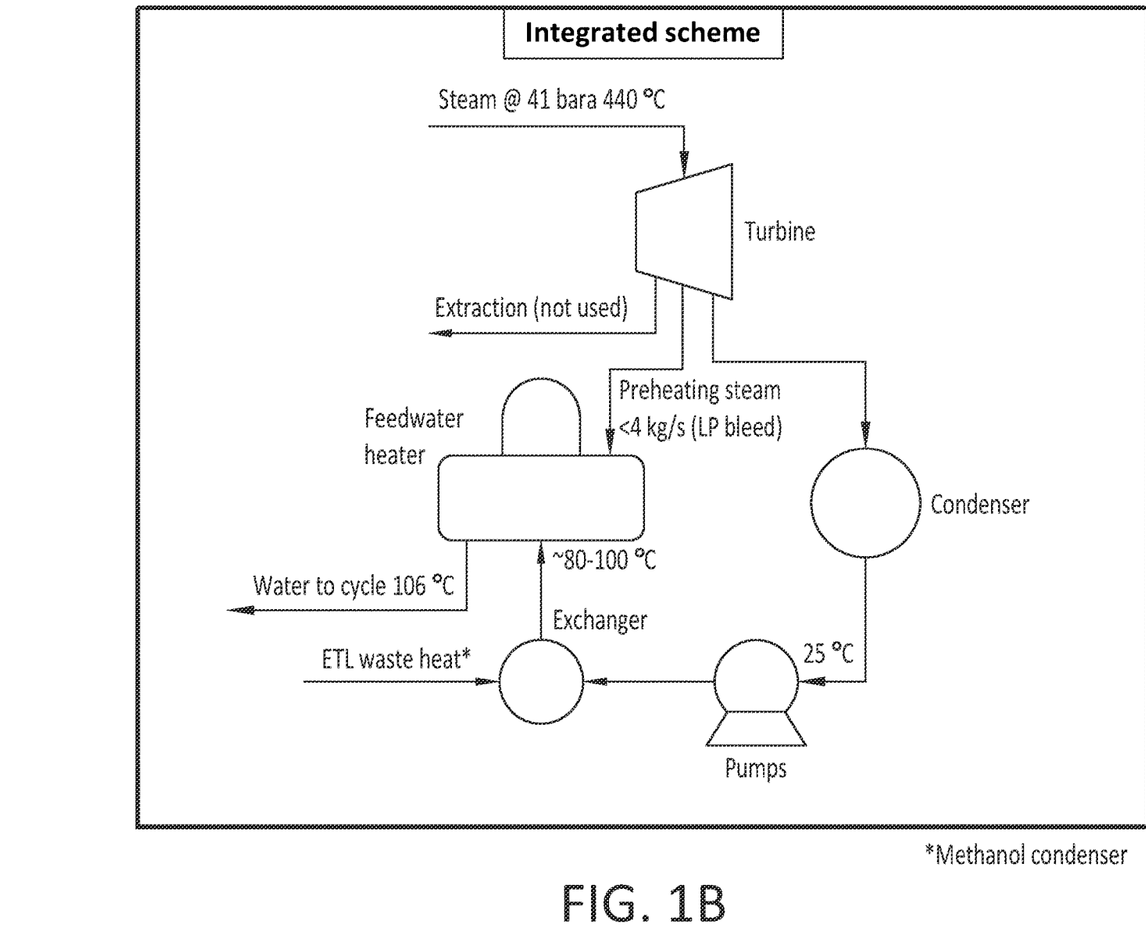

FIG. 1B shows a modified operational scheme according to an embodiment of the present disclosure, with heat integration from the ETL (or another plant with excess relatively low grade waste heat), where the operational scheme is the same, except that the condensed water (e.g., at 25° C.) is not preheated fully by the LP preheating working fluid bleed from the turbine, but is first preheated by low grade waste heat provided by the ETL plant (e.g., heat provided through synthesis and/or condensation of the methanol, or another chemical product produced by the partner plant, through an exothermic reaction). This preheating using heat available from the ETL plant preheats the condensed water of the thermodynamic power cycle to a value that is intermediate the cold and preheated values (higher than 25° C. and lower than 106° C.) seen in FIG. 1A. Final preheating (e.g., to 106° C.) of the condensed water stream can be provided by a LP or MP working fluid bleed from the turbine, although the flow rate of such LP or MP bleed will be significantly less than was needed in FIG. 1A, because most of the preheating has already been accomplished by the waste heat provided from the ETL plant. FIGS. 1A-1B thus illustrate the general principal being applied in the present disclosure.

Figure 4:
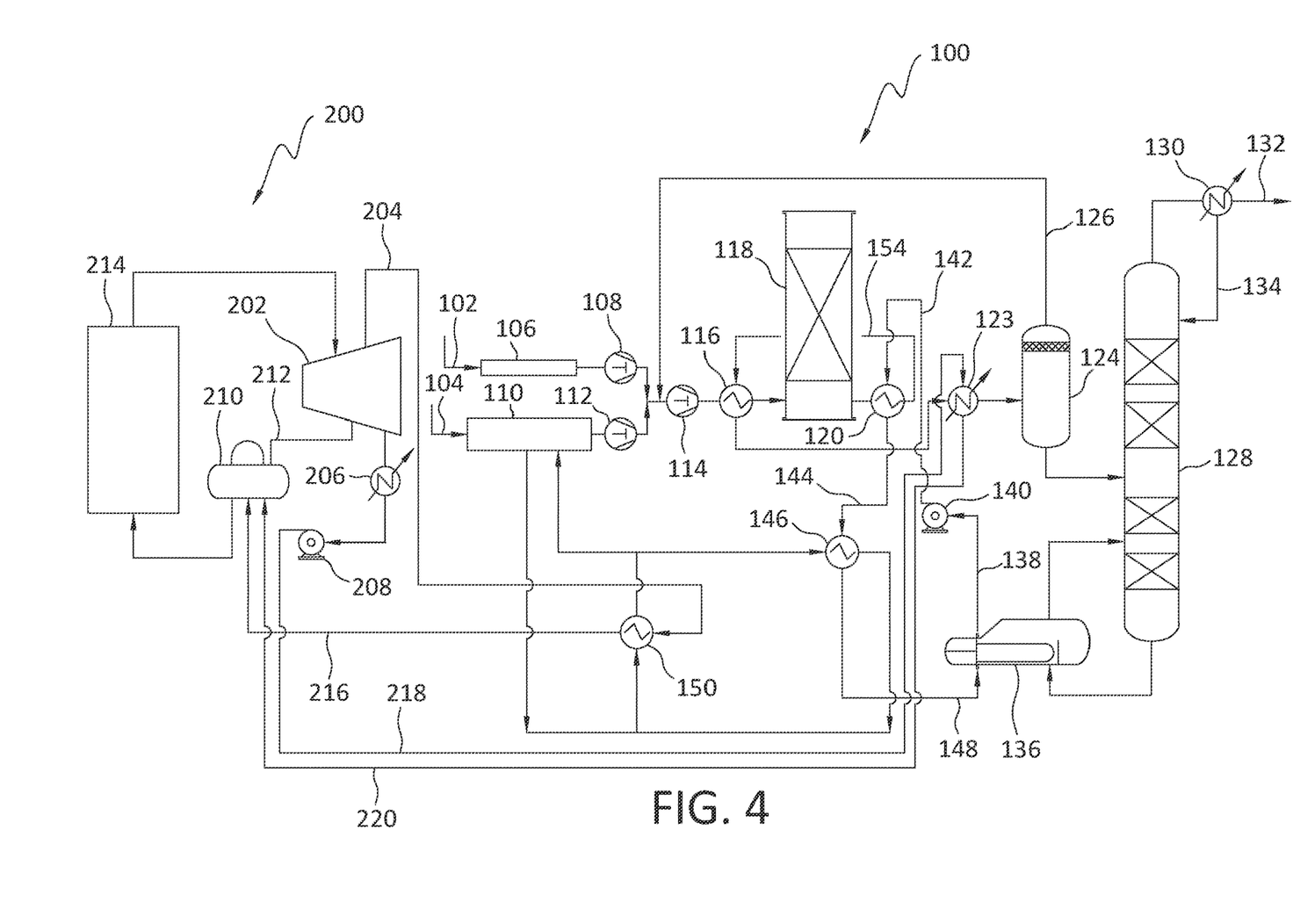
FIG. 4 is a simplified diagram showing another embodiment of how heat (more accurately both waste heat and higher-grade heat from steam or another working fluid) may be integrated between an ETL plant and a partner plant that includes a thermodynamic power cycle that generates steam or another working fluid.

Referring to FIG. 4, ideally, the waste heat stream 220 of the ETL plant 100, would be sufficient for the needs of the water pre-heater 210 of the power cycle partner plant, minimizing or altogether eliminating the need for the bleed stream 212, and freeing the higher-quality steam or other working fluid stream to more beneficial uses (e.g., electrical generation, use for heating in the ETL plant, or other). If, however, the waste heat stream 220 does not sufficiently heat the water in pre-heater 210, the bleed stream 212 can be used to fill the need. More information concerning this embodiment will be described below.

A distillation process that may benefit from heat integration as described herein is described in U.S. Pat. No. 10,960,349, issued Mar. 30, 2021, belonging to applicant, which patent is herein incorporated by reference in its entirety. The distillation process described is a highly energy-intensive process, requiring significant heat in the separation process, particularly in the reboiler of the distillation column. Steam or other working fluid generated for use in a turbine in the power cycle of a typical electrical power generation plant is particularly well suited for use in providing the necessary heat to the reboiler of such a distillation process. There is also a need for heat in the $CO_2$ capture unit of such an ETL process. There is also potentially a need for heat (or steam, in which case both the steam itself as well as its thermal energy could be utilized) in the $H_2$ generation unit, depending on technology selected.

Of course, there is always incentive to integrate available heat internally, within any given process, to maximize energy efficiency. For example, referring to FIG. 2, one possible scenario for internal heat integration is shown within the context of an exemplary ETL plant. The ETL plant 100 comprises two feed streams 102, 104. The first feed stream 102 may comprise water fed into an electrolysis unit 106 resulting in the production of hydrogen gas. The $H_2$ may then be compressed in a compressor 108. The second feed stream 104 may be comprised of a gas containing $CO_2$ fed into a $CO_2$ capture unit 110. The $CO_2$ is compressed in a compressor 112, and then mixed with the compressed hydrogen stream in a syngas compressor 114. The resulting syngas may be fed into a heat exchanger 116, which provides heated syngas to a methanol reactor 118, and a recycle or bypass portion to a condenser 122.

Figure 2:
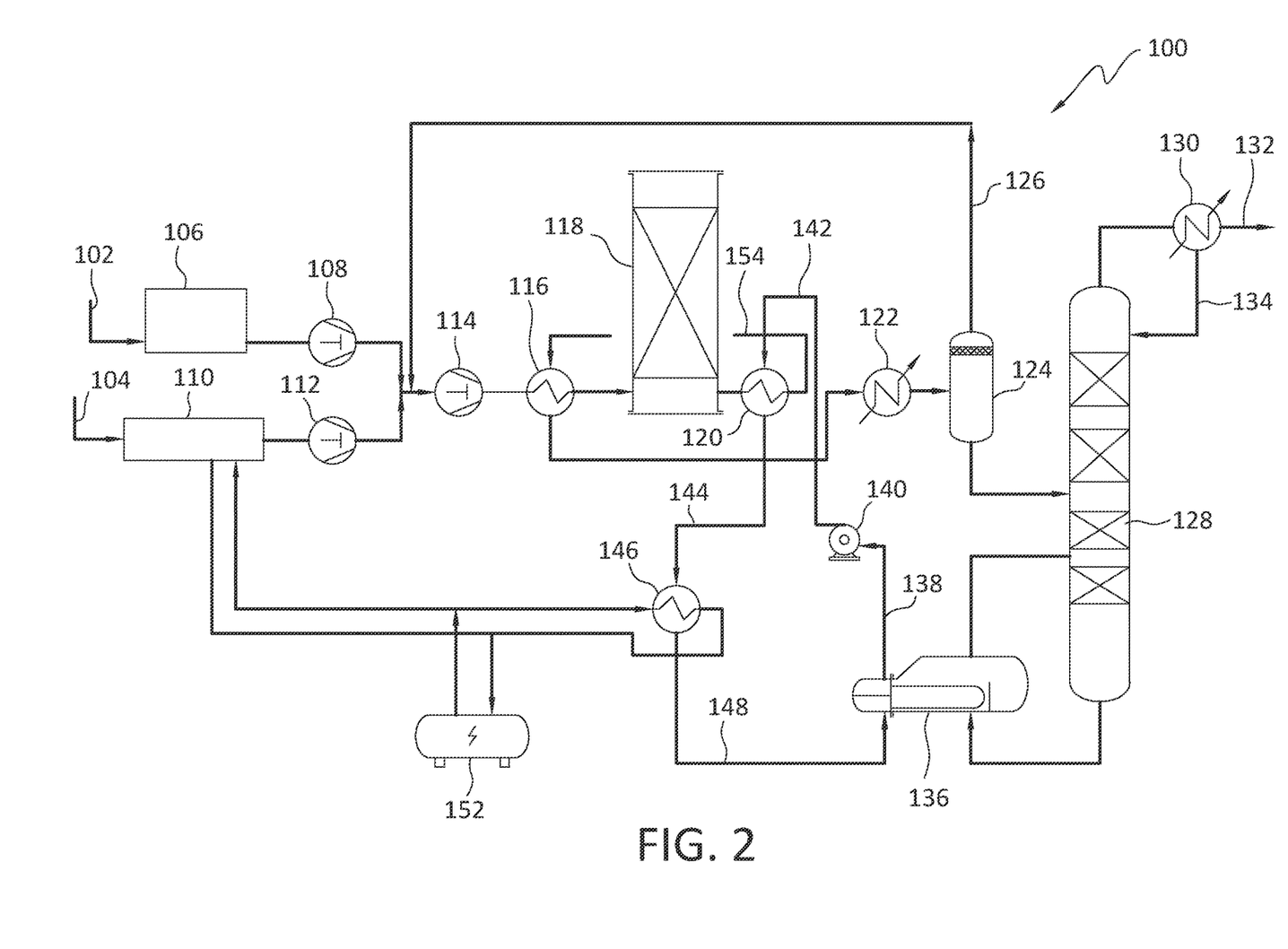
FIG. 2 is a simplified diagram of an exemplary ETL plant with internal heat integration according to the present disclosure.

The stream leaving condenser 122 enters a catch pot 124 where the top fraction 126 is recycled back to the syngas compressor 114 and the bottom fraction is fed to a distillation column 128. The top fraction from the distillation column 128 can be fed to a condenser 130, with a portion being recycled back into the distillation column 128 as reflux stream 134, with the high purity distillate methanol stream 132 being sent to storage or other desired use. The bottom outlet of the distillation column 128 is fed to a reboiler 136 which returns the heated distillation bottom fraction to the distillation column 128.

The internal heat integration of the ETL plant 100 shown in FIG. 2 functions to reduce the outside heat required in the reboiler 136. The reboiler 136 has a cold outlet stream 138, which is fed to a pump 140 to increase pressure. The stream 142 leaving the pump 140 is fed to a heat exchanger 120, which increases the temperature. The heat exchanger 120 receives heat by being connected to the outlet of the methanol synthesis reactor 118. For example, heat exchanger 120 may cool the methanol product, while transferring waste heat from the exothermic reaction carried out in reactor 118 to stream 144. Further cooling and condensation of the methanol product stream may be carried out further downstream. The reaction of syngas to methanol is exothermic, which allows the outlet from reactor 118 fed into heat exchanger 120 to heat the stream 142 coming from the pump 140, thus making more efficient use of heat energy within the system, to preheat stream 142, while lowering the temperature of the recycled methanol 154 going back into the methanol reactor 118, to regulate the reaction temperature.

After exiting the heat exchanger 120, a resulting midrange temperature stream 144 is fed to another heat exchanger 146. This heat exchanger 146 raises the temperature of the heated fluid stream 148 to a sufficiently high temperature for use in heating the distillation bottoms materials in the reboiler 136.

Figure 3:
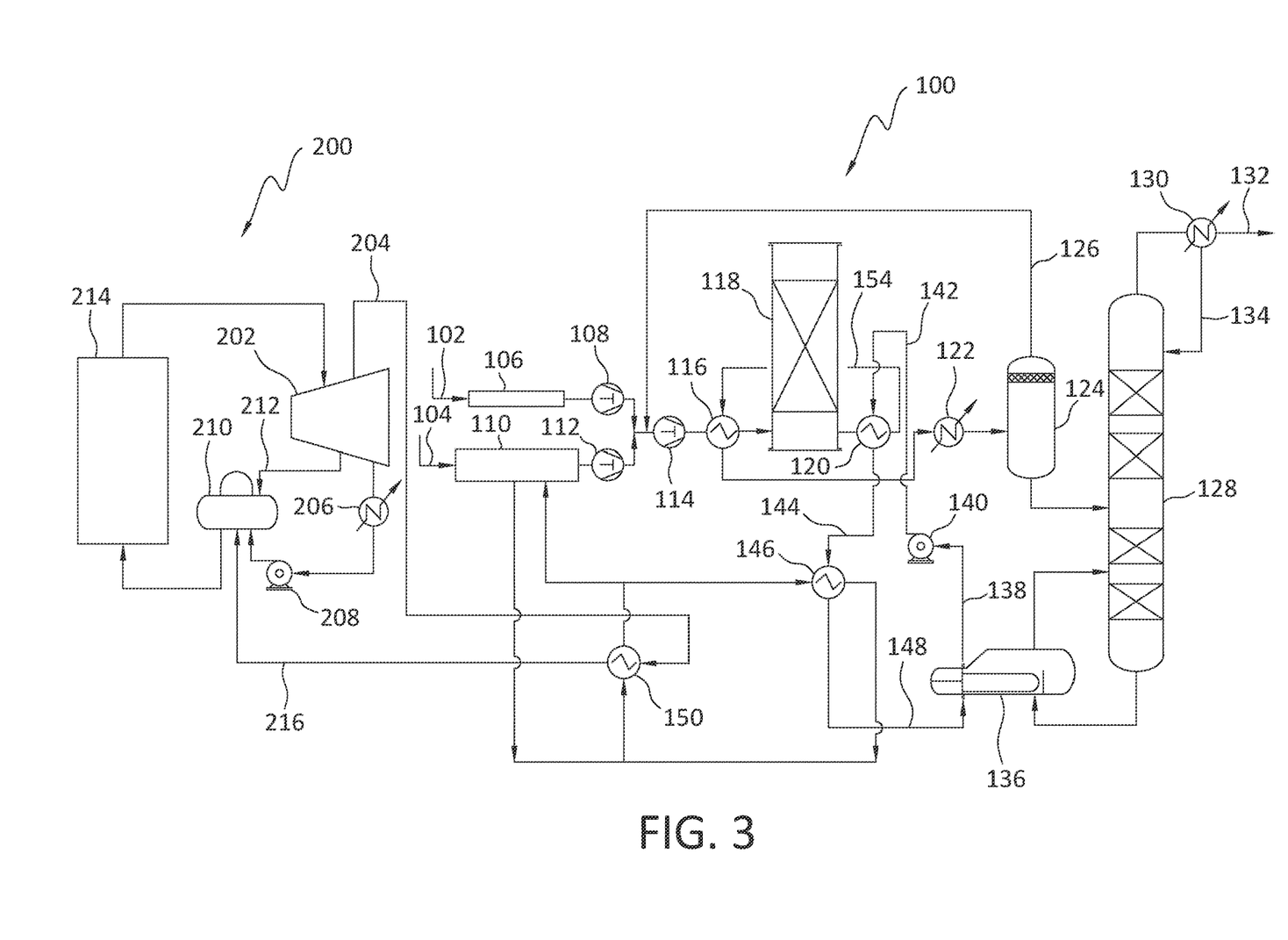
FIG. 3 is a simplified diagram showing one embodiment of how heat may be integrated between an ETL plant and a partner plant that includes a thermodynamic power cycle that generates steam or another working fluid.

The heat exchanger 146 may use the heat generated from an electric steam or other heating medium generator 152 (e.g., direct use of steam or other heating medium). Capturing $CO_2$ requires energy, e.g., provided as steam. The plant design shown in FIG. 2 is configured to recover as much heat as practical from the reaction (through heat exchanger 120), and make-up the rest with steam or other heating medium generated electrically. Note that a conventional natural-gas or other fuel powered boiler is not shown as being used to generate the needed steam or other heating medium, as this would produce $CO_2$ emissions, which is undesirable for a plant intended to capture $CO_2$ emissions and convert that carbon to a value added product. The loop defined by streams 138, 142, 144, 148 of FIG. 2 is the heating medium distribution system, which allows reception of the heat from the heat generating sources (the exothermic process in reactor 118, the electrical steam or other heating medium generator 152, but most preferably, and ultimately heat from the power cycle as shown in FIG. 3), for ultimate distribution to user modules where needed. In FIG. 2, the heating medium from the generator 152 is shown as being directly fed to the $CO_2$ capture unit 110, although it could use the internal loop as well (although this would be less efficient). It will be apparent that heat from the power cycle can also be used in the $CO_2$ capture unit 110, to perform mechanical work (e.g., in a syngas or other compressor), etc.

In any case, the use of internal heat integration by using waste heat from the methanol synthesis reactor 118 to preheat the reboiler cycling fluid (flowing in the loop defined by 138, 142, 144, 148) increases the efficiency of the ETL plant 100. Even with such internal heat integration, there is still a need for the electric generator 152, as shown in FIG. 2, to complete heating of the fluid used to reboil the distillation column bottoms fraction in reboiler 136. If the ETL plant were located adjacent to another plant that could provide such a high energy steam or other heating medium stream, the electric heating medium generator could be eliminated. Embodiments providing such are described below.

For example, as shown in FIG. 3, external heat integration may be introduced, and the electric working fluid generator 152 may be replaced with a heat exchanger 150 connected to a partner plant 200. The partner plant 200 includes a power cycle, such that it generates working fluid (e.g., steam), and a bleed stream of such working fluid may replace the generator 152 by providing steam or another working fluid as a heating medium at near optimal conditions, in exchange for waste heat from the ETL plant, used to preheat the condensed water or other working fluid of the power cycle. The working fluid diverted from the power cycle is better used in providing the needed heat to the reboiler 136 (and/or $CO^2$ capture unit 110 or $H_2$ generation unit 106) of the ETL, plant 100 than for reheating condensed water or other working fluid of the power cycle (or even generating electricity). Similarly, at least some of the waste heat from the methanol condenser at the outlet of the reactor 118 of the ETL plant 100 is beneficially used in preheating the condensed water or other working fluid of the power cycle of plant 200, e.g., even where some such heat may first be used internally within the ETL plant, as shown in the Figures.

Currently, a partner plant 200 will generate electricity which can their be bought by an ETL plant 100 which converts the electricity to steam or another heating medium (e.g., see the generator 152 of FIG. 2). If a portion of the steam or other working fluid is instead diverted from the power cycle of partner plant 200, rather than converting it to electricity and then back to steam (which is incredibly inefficient), energy is saved, and both processes become more efficient. For example, when converting steam (or another working fluid) to electrical energy (e.g., in turbine 202 of a power cycle), about two-thirds of the energy is lost in making such a conversion, and an additional amount is lost when converting electricity back to steam (or another heating medium), in an electric steam generator.

Referring to FIG. 3, which shows heat integration (e.g., steam integration) from the power plant to the ETL plant, the electrical generating partner plant 200 comprises a turbine 202, a condenser 206, a pump 208, a water pre-heater 210, and a working fluid generator (e.g., a boiler) 214. The power cycle of plant 200 is made up of these components. Although not shown, a pump may also be provided downstream from the water pre-heater 210 to increase the pressure of the loop to high pressure (e.g., about 40 bara or more) prior to heating, boiling and super-heating in the boiler (214). While one pre-heater 210 is shown in the figure, it will be appreciated that multiple pre-heaters may be used, e.g., in relatively large power cycles where multiple bleeds and multiple pre-heaters may sometimes be provided. Such configurations are of course within the scope of the present disclosure. In addition, those of skill in the art will appreciate that feedwater heaters (water pre-heaters) in steam power plants can be of the 'open' or 'closed' type. In the open type, the LP bleed steam and condensate are mixed directly. Closed feedwater heaters are similar to traditional heat exchangers where heat is transferred between two streams without mixing the streams, allowing heat transfer at differing pressures. The present disclosure of course contemplates use of either type (open or closed) of feedwater heater. One or more working fluid bleed streams may also be provided, diverting some of the steam or other working fluid from electrical generation in turbine 202 to other uses. Such bleed streams may be at any of various desired pressures, e.g., a low-pressure (LP) bleed stream, a medium-pressure (MP) bleed stream, etc. To integrate the partner plant 200 with the ETL plant 100, a portion of working fluid (e.g., a MP bleed stream) is diverted from turbine 202 and introduced to the heat exchanger 150 as a heating medium. By way of example, the MP bleed stream 204 may be between 150-200° C. and at a pressure of 5-15 bara. To utilize as much energy as possible, the working fluid is condensed in heat exchanger 150 and is returned as a liquid condensate. This exiting stream 216 is returned to the water pre-heater 210, where the remaining heat therein can be used to preheat water coming from the condenser 206 and pump 208, before sending such preheated water to the working fluid generator 214, for starting the power cycle again.

FIG. 4 shows a more complex heat integration between plants 100 and 200, showing heat transfer from the ETL plant to the power cycle, in addition to the heat integration (e.g., steam integration) shown in FIG. 3. For example, condensed, pressurized water at 20-30° C. (or other relatively low condensed temperature) is supplied via a pump 208 as a cold stream 218 to heat exchanger 123 of ETL plant 100. The water is heated to, for example, about 100° C. using heat available from the exothermic reaction (e.g., methanol synthesis) conducted in reactor 118, and the heated stream 220 is fed back to the water pre-heater 210 of electrical generation plant 200. By way of example, the reactor effluent stream which is the opposing fluid in the heat exchanger 123 that is used to heat stream 218 may enter heat exchanger 123 at 110° C. (e.g., under pressure) and may exit at 40° C. This integration significantly lowers the needed flowrate for the bleed stream 212, which is a high-quality stream of significant value (e.g., it could be used to generate additional electricity, provide heat to reboiler 136 of ETL plant 100, used in $CO_2$ capture unit 110, or otherwise). It also lowers the cooling required to fully cool the stream from heat exchanger 123 to the catch pot 124. Although such cooling water stream is not shown in the figure, the needed flowrate of such cooling water is significantly reduced. The present embodiment replaces the need for most of this high value bleed stream with lower value heat from the heat exchanger 123 (with heat provided from the exothermic reaction of methanol synthesis), provided by ETL plant 100. The returning heated stream 220 is entirely capable of achieving the majority of the required preheating of the stream exiting condenser 206, with any final further heating accomplished by a reduced flowrate bleed stream 212, as shown.

Examples

Figure 5B:
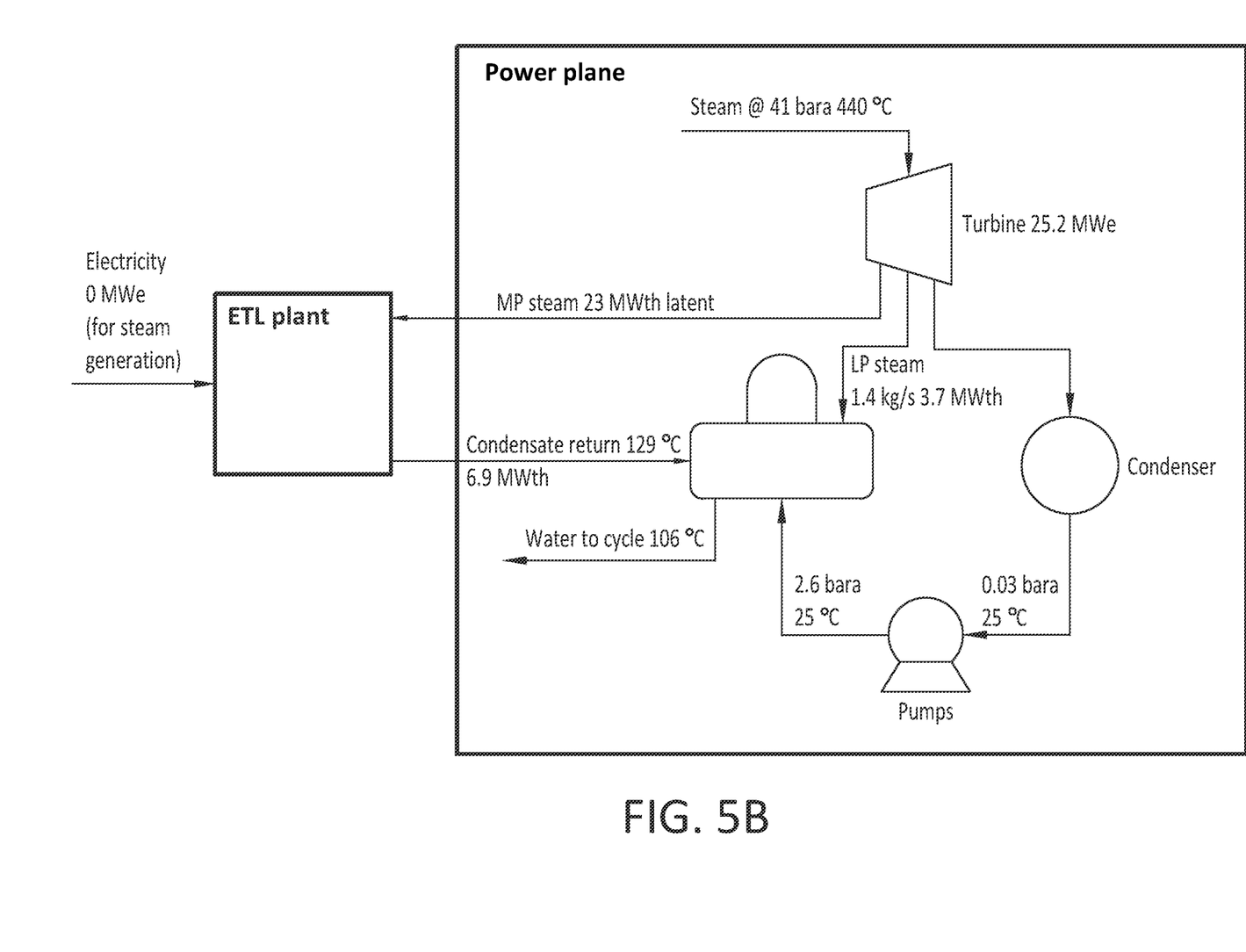
FIG. 5B illustrates a specific example of heat integration via steam or other working fluid, showing elimination of the need to import electricity to the ETL plant. Even though electricity generated in the turbine is reduced as a consequence of diversion of a portion of the working fluid, the net electricity export is increased substantially compared to the baseline configuration of FIG. 1A that includes no integration.
Figure 5C:
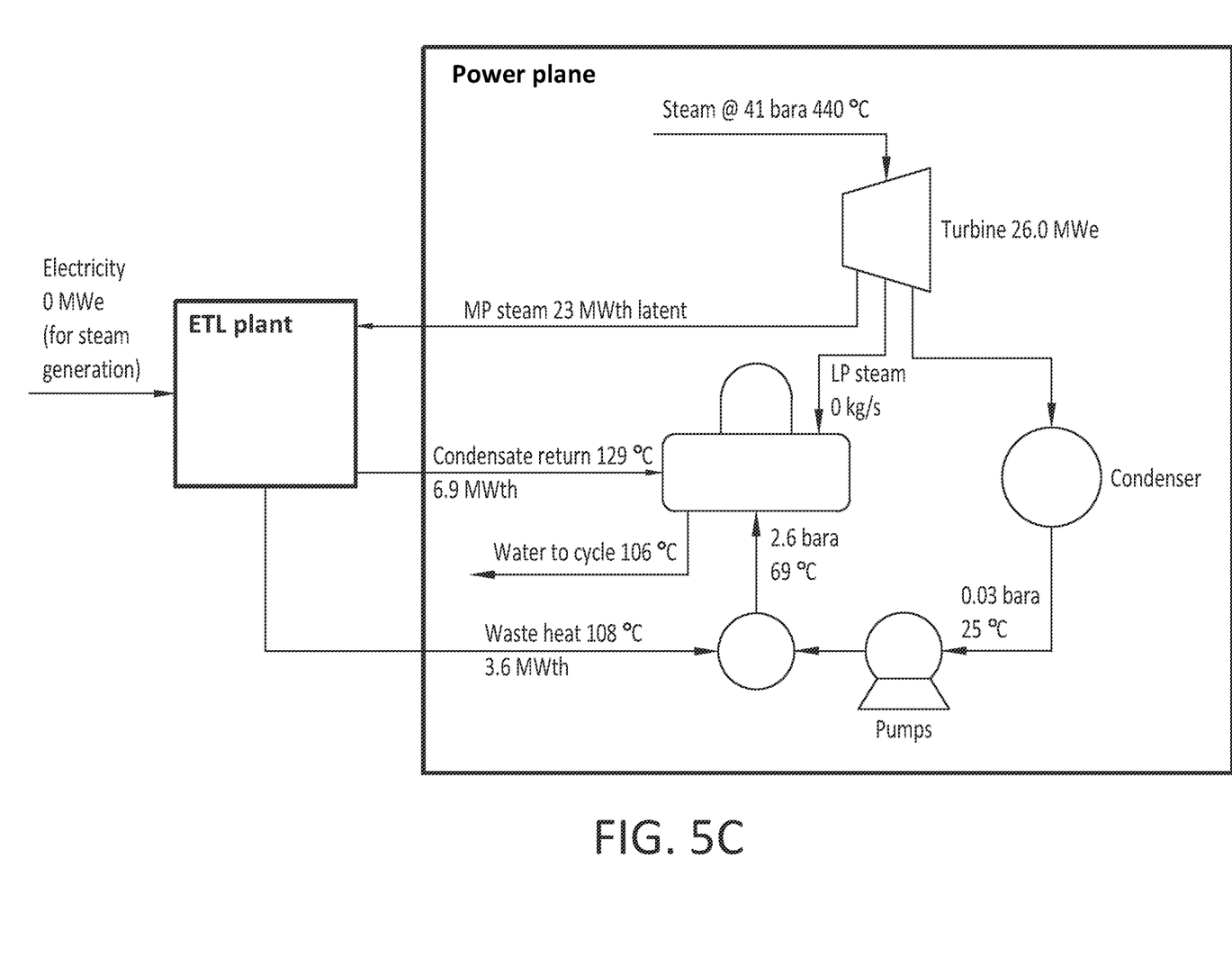
FIG. 5C illustrates a specific example of both heat integration via steam or other working fluid and waste heat integration, showing further increase in the net electricity export as compared to the baseline configuration of FIG. 1A that includes no integration.

FIGS. 5A-5C illustrate three specific examples, e.g., based on the configurations shown in FIGS. 3-4, focusing on the increased efficiencies achieved, as a result of such heat integration. The examples shown can be compared to FIG. 1A, for a "baseline" comparison. While steam is used in the examples, it will be apparent that other working fluids/heating media are of course also possible. The increased efficiency, including net electrical power generation, provided in FIGS. 5A-5C is provided without any increase in flowrate of working fluid into the power cycle system (the flowrate of steam at 440° C. and 41 bara remains unchanged). The baseline operation as shown in FIG. 1A generates 32 MW at full load. The example shown in FIG. 5A only needs to divert 0.4 kg/s of LP steam bleed in order to achieve the target 106° C. water to cycle, because of the waste heat provided by the ETL plant 100. For example, as shown in FIG. 5A, the stream returned to the feedwater heater (e.g., pre-heater 210) is able to be preheated to 98° C. (rather than the 25° C. in the scenario of FIG. 1A), using heat integrated from the ETL plant. The LP bleed flowrate is reduced from 4 kg/s to only 0.4 kg/s (a 90% reduction). As a result, the fraction of the 440° C. 41 bara steam that is fully utilized for electrical generation in the turbine is increased, resulting in a 5.9% increase in power generation (33.9 MW vs. 32 MW). As shown in FIG. 5A, the ETL plant is using 23.5 MW of electrical power for steam generation, providing a net electricity export of 33.9−23.5=10.4 MW. The electric steam boiler is assumed to operate at 98% efficiency. The baseline configuration of FIG. 1A provides a net electricity export of 32−23.5=8.5 MW. FIG. 5A thus represents an increase of 22% in net electricity export. The embodiment shown in FIG. 5A could be described as providing "heat integration".

FIG. 5B shows an embodiment that could be described as providing "steam integration". 23 MW of thermal energy in the form of steam is provided from the power plant, eliminating the need for the steam generator in the ETL plant. Even though this reduces the electricity generated in the turbine, the net electricity export is increased, as compared to the baseline of FIG. 1A (and even to the heat integration shown in FIG. 5A). As shown in FIG. 5B, the steam condensate is returned to the drum after such steam is used in the ETL plant, providing significant heat for use in preheating the condensate in the water pre-heater 210. As a result, the flowrate of the LP bleed stream used to complete the desired pre-heating is reduced to 1.4 kg/s (compared to the 4 kg/s in FIG. 1A). The turbine is still able to generate 25.2 MW of electrical power, and no electrical power is consumed by any steam generator in the ETL plant (as it has been eliminated). The net electricity export is thus 25.2−0=25.2 MW, which represents a 196% increase nearly a tripling of the original 8.5 MW baseline).

FIG. 5C shows an embodiment providing both "steam integration" and "heat integration", combining the integrations seen in FIGS. 5A and 5B. In this scenario, the LP bleed stream needed to achieve final pre-heating of the condensate in pre-heater 210 has been eliminated (flowrate of 0 kg/s), and the turbine is able to generate 26 MW of electrical power, so that net electricity export is thus 26−0=26 MW, which represents a 205% increase (more than a tripling of the original 8.5 MW baseline).

While FIGS. 5A and 5C do not illustrate such, there is also a significant reduction in the need for cooling water in the ETL plant (e.g., a 10-20% reduction in the cooling water flowrate needed for cooling and condensing the produced methanol).

While the examples and much of the disclosure describe heat integration between an electrical power generation plant and a chemical synthesis plant generating waste heat through an exothermic synthesis reaction, it will be appreciated that the disclosure is not limited to such. For example, as noted herein, a plant may operate a thermodynamic power cycle without actually generating any electricity, still exhibiting a need to reheat the condensed working fluid as part of such a cycle (whether an electrical power generating turbine is present or not). By way of example, this may be the case especially for green field sites, where the power cycle might not produce electricity. There might be sites with waste heat from industry, where it is more economical to use all the heat as thermal energy. This might be the case for a ferrosilicon or other plant in some parts of the world (e.g., Iceland, Norway, etc.). For example, the waste heat recovery unit would generate steam or another working fluid/heating medium which could be used for $CO_2$ capture, to run a compressor, for use in distillation, for district heating of the industry area, heating in a nearby town and/or possibly other industries, such as fish farming. It will be apparent that some such specific cases might not produce electricity, and the present disclosure is not limited to such.

In some such cases, heat integration from an ETL plant or other chemical synthesis plant to the power cycle may not be possible, as the returning condensate in the power cycle may already be hotter than the temperature of the chemical synthesis plant waste heat stream, such that heat integration may be one way only (e.g., use of generated steam or other working fluid in the ETL or other chemical synthesis plant, without necessarily any return of waste heat to the plant running the power cycle).

Accordingly, features of the disclosed embodiments may be combined or arranged for achieving particular advantages as would be understood from the disclosure by one of ordinary skill in the art. Similarly, features of the disclosed embodiments may provide independent benefits applicable to other examples not detailed herein.

It is to be understood that not necessarily all objects or advantages may be achieved under any embodiment of the disclosure. Those skilled in the art will recognize that system and method may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to make or use a heat, steam and/or other heated working fluid integration under principles of the present disclosure. It will be understood by the skilled artisan that the features described may be adapted to other systems and processes. Hence this disclosure and the embodiments and variations thereof are not limited to methanol synthesis processes or to specific partner plants but can be utilized by integrating heat between any exothermic chemical process that generates waste heat with any partner process that generates high value steam or another high value working fluid/heating medium.

Although this disclosure describes certain exemplary embodiments and examples of heat integration, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. As used herein, the term "between" includes any referenced endpoints. For example, "between 2 and 10" includes both 2 and 10.

The invention claimed is:

1. A system for heat integration between (i) a partner plant which generates steam or another working fluid as part of a power cycle and (ii) an emissions to liquid (ETL) plant which produces heat from an exothermic reaction, the system comprising:
  a steam or other working fluid generator associated with the partner plant;
  a turbine associated with the partner plant, the turbine being configured to receive steam or other working fluid from the steam or other working fluid generator;
  a condenser associated with the partner plant, the condenser being configured to receive spent steam or other working fluid from the turbine and to cool and/or condense the spent steam or other working fluid;
  a pump associated with the partner plant, the pump being configured to receive the condensed steam or other working fluid from the condenser;
  a water pre-heater, either of an open or a closed type, associated with the partner plant, the water pre-heater being configured to receive the condensed steam or other working fluid from the pump;
  first and second bleed streams from the turbine;
  wherein the second bleed stream from the turbine is fed to a heat exchanger of the ETL plant where heat from the second bleed stream is used by the ETL plant to heat a bottoms condensate fraction from a distillation column in a reboiler associated with said distillation column, the heat exchanger returning a cold stream to the water pre-heater associated with the partner plant, wherein the reboiler is configured to obtain heat, directly or indirectly, from the exothermic reaction conducted within a reactor of the ETL plant.

2. The system as recited in claim 1, wherein the power cycle is used to produce electricity.

3. The system as recited in claim 1, wherein the power cycle is a power cycle that is not used to produce electricity.

4. The system as recited in claim 1, wherein steam or other working fluid from the power cycle is used to run mechanical equipment, for capturing $CO_2$, and/or for $H_2$ generation.

5. The system as recited in claim 1, wherein the first bleed stream is a low pressure bleed stream.

6. The system as recited in claim 1, wherein the second bleed stream is a medium pressure bleed stream.

7. The system as recited in claim 1, wherein the condenser is a seawater condenser.

8. The system as recited in claim 1, wherein the first bleed stream from the turbine is of a lesser flow rate than would be required if the heat exchanger of the ETL plant did not return a cold stream to the water pre-heater associated with the partner plant.

9. A system for heat integration between (i) a partner plant which generates steam or another working fluid as part of a power cycle and (ii) an emissions to liquid (ETL) plant which produces heat from an exothermic reaction, wherein:
   a bleed stream taken from a turbine associated with the power cycle of the partner plant is fed into a heat exchanger of the ETL plant for heating a bottoms condensate fraction from a distillation column in a reboiler associated with said distillation column of the ETL plant, the heat exchanger returning a cold stream to a water pre-heater of the partner plant, wherein the reboiler is configured to obtain heat, directly or indirectly, from the exothermic reaction conducted within a reactor of the ETL plant;
   a pump associated with the partner plant which supplies a condensed cold stream from the turbine associated with the power cycle of the partner plant to a heat exchanger associated with the partner plant, the heat exchanger being configured to receive heat from the exothermic reaction of the ETL plant and exchange the heat from the exothermic reaction of the ETL plant as a hot stream to the cold stream from the turbine associated with the partner plant to heat said cold stream, and return a preheated stream to a water pre-heater associated with the partner plant for final heating of a steam or other working fluid in a steam or other working fluid generator associated with the power cycle of the partner plant.

10. The system for integration of claim 9, wherein the hot stream is a low-quality working fluid stream and minimizes or reduces a need to use a higher-quality bleed stream, relative to the low-quality working fluid stream, from the turbine in the water pre-heater.

11. The system for integration of claim 9, wherein the bleed stream is a medium pressure bleed stream.

12. The system for integration of claim 9, wherein steam or another working fluid from the power cycle is also or alternatively used to provide heat to a stripper of a carbon capture unit and/or used to provide steam or heat to an $H_2$ generation unit.

13. An ETL (emissions to liquid) plant comprising:
   two feed streams,
   wherein the first feed stream contains water from which hydrogen is produced in an electrolysis unit, and the second feed stream comprises $CO_2$;
   an electrolysis unit, which is configured to receive water from the first feed stream and generate hydrogen gas from the water;
   a $CO_2$ capture unit, which is configured to receive $CO_2$ from the second feed stream;
   at least one compressor, wherein the at least one compressor is configured to compress at least one of the hydrogen gas, the $CO_2$, and/or a mixture of the two gases;
   a plurality of heat exchangers, at least one heat exchanger being configured to receive a mixture of the hydrogen gas and the $CO_2$ from the at least one compressor;
   a reactor, which is configured to receive a heated mixture of the hydrogen gas and the $CO_2$ from the heat exchanger and within which an exothermic reaction is conducted;
   a catch pot, which is configured to receive a bypass portion of the heated mixture of the hydrogen gas and the $CO_2$ that is not fed into the reactor;
   a catch pot top fraction, which is configured to be recycled back into the at least one compressor that is configured to compress at least one of the hydrogen gas, the $CO_2$, and/or a mixture of the two gases;
   a distillation column, which is configured to receive a bottom fraction from the catch pot;
   a condenser, which is configured to receive a top fraction from the distillation column:
   a reflux stream, which is a portion of the top fraction from the distillation column that is configured to be recycled back into the distillation column after leaving the condenser;
   a distillate stream sent to storage, which comprises a high purity liquid chemical, isolated from the distillation column;
   a reboiler, which is configured to receive a bottom fraction from the distillation column, to return a heated bottom fraction from the distillation column to the distillation column, and wherein the reboiler obtains heat, directly or indirectly, from the exothermic reaction conducted in the reactor;
   and a source of steam or other heating medium generated electrically, which is configured to provide heat to the reboiler in order to complete heating a fluid used to re-boil the bottom fraction from the distillation column in the reboiler when the heat obtained by the reboiler from the exothermic reaction conducted in the reactor is not sufficient.

14. The ETL plant of claim 13, wherein the exothermic reaction conducted in the reactor is a methanol synthesis reaction.

15. The ETL plant of claim 13, wherein the source of steam or other heating medium generated electrically comes from an electric steam generator.

16. A system for internal heat integration within a plant comprising:
   a reactor within which an exothermic reaction is conducted;
   a reboiler for reheating a bottoms condensate fraction from a distillation column;
   a pump configured to receive a cold stream from the reboiler and to increase the pressure of the cold stream from the reboiler;
   first and second heat exchangers;
   wherein the first heat exchanger is connected to an outlet of the reactor and is configured to receive from the pump the cold stream from the reboiler; and
   wherein the second heat exchanger is configured to receive an outlet stream from the first heat exchanger which has been heated to an increased temperature relative to the cold stream and to further heat the outlet stream to a desired temperature before feeding the heated outlet stream to the reboiler.

17. The system for internal heat integration of claim 16, wherein the plant is an emissions to liquid (ETL) plant.

18. The system for internal heat integration of claim 16, wherein the exothermic reaction conducted in the reactor is a methanol synthesis reaction.

19. The system for internal heat integration of claim 16, wherein the second heat exchanger utilizes steam or another working fluid to produce the heated outlet stream.

20. The system as recited in claim 16, wherein the reboiler is configured to obtain heat, directly or indirectly, from the exothermic reaction conducted within the reactor.

* * * * *